United States Patent
Mitra et al.

(10) Patent No.: US 7,507,424 B2
(45) Date of Patent: Mar. 24, 2009

(54) NATURAL IMMUNOSTIMULANT COMPOSITIONS, METHODS FOR OBTAINING THE SAME AND PHARMACEUTICAL FORMULATIONS THEREOF

(75) Inventors: Shanker Kumar Mitra, Kamataka (IN); Ekta Saxena, Kamataka (IN); Mallikarjun Narayan Dixit, Kamataka (IN)

(73) Assignee: MMI Corporation, Cayman Islands (VG)

( * ) Notice: Subject to any disclaimer, the term of this patent is extended or adjusted under 35 U.S.C. 154(b) by 355 days.

(21) Appl. No.: 10/831,101

(22) Filed: Apr. 26, 2004

(65) Prior Publication Data

US 2005/0238736 A1  Oct. 27, 2005

(51) Int. Cl.
*A61K 36/00* (2006.01)

(52) U.S. Cl. .................... 424/725; 424/774; 424/775

(58) Field of Classification Search .............. None

See application file for complete search history.

(56) References Cited

U.S. PATENT DOCUMENTS 6,455,077 B2 *  9/2002  Katiyar et al. .............. 424/725

FOREIGN PATENT DOCUMENTS

JP  2001-192317 A  *  7/2001

OTHER PUBLICATIONS

Ahmed et al. (Fitoterapia (1986), vol. 57, No. 6, pp. 457).*
Ali et al. (Pharmaceutical Biology (2001), vol. 39, No. 1, pp. 43-46).*
Mishra et al. (Indian Journal of Physiology and Pharmacology (1964), vol. 8, No. 3, pp. 181-188).*
Sajid et al. (Phytotheraphy Research (1996), vol. 10, pp. 178-180).*
Ahmad (Lancet Infectious Diseases (2005), vol. 5, No. 9, p. 537).*
http://www.merriam-webster.com/dictionary/aqueous—accessed Jul. 2008.*

* cited by examiner

*Primary Examiner*—Susan C Hoffman
(74) *Attorney, Agent, or Firm*—Darby & Darby P.C.

(57) ABSTRACT

A natural immunostimulant composition for the treatment of immunodeficiency, the composition comprising extract of plant *Symplocos racemosa* and/or plant *Prosopis glandulosa* and a pharmaceutically acceptable carrier is disclosed. Also disclosed are methods for obtaining the plant extract, methods for preparing the composition and methods of treating diseases related to immunodeficiency.

19 Claims, 8 Drawing Sheets

NATURAL IMMUNOSTIMULANT COMPOSITIONS, METHODS FOR OBTAINING THE SAME AND PHARMACEUTICAL FORMULATIONS THEREOF

FIELD OF THE INVENTION

This invention relates to a natural immunostimulant composition, more particularly, a natural immunostimulant composition comprising extract of plant *Symplocos racemosa* and/or plant *Prosopis glandulosa* and a pharmaceutically acceptable carrier, methods of obtaining the same, pharmaceutical formulations thereof and methods of treating immunodeficiencies in animals including humans using said natural immunostimulant composition.

BACKGROUND OF THE INVENTION

Immunomodulation is a process that alters the immune system of an organism by interfering with its functions. This process results in immunostimulation, an enhancement of immune reaction or immunosuppression that results in the reduction of resistance against infections and stress, which could be caused due to environmental or chemotherapeutic factors.

As a therapeutic concept, immunostimulation has long been known in medicine. It is defined as the injection of substances which themselves have only weak, if any, antigenic effect, but are nevertheless able to induce the body's own defence mechanisms in a specific or even non specific manner.

In the recent years, the research on immunomodulators has considerably advanced to form into a new field knowledge known as immunopharmacology. Immunomodulation is a strategy for overcoming incurable autoimmune diseases such as cancer, arthritis, allergies and AIDS. The immune system is supposed to provide both the theoretical and therapeutic disorders of many chronic disorders. In today's world, extensive exposure to pollutants and xenobiotics has resulted in the emergence of atypical immune deficiencies that has changed the strategy for treating patients. Consequently, immunology has come to play a greater role.

To overcome the challenges posed by immunological deficiencies, major research activities have been directed at developing new pharmaceutical formulations, which are in turn aimed at modulating immune responses as well as stimulating immune defence mechanisms. The recent research is also aimed at safe and effective treatments for immunological deficiencies.

RELATED ART

U.S. Pat. No. 6,548,086 to Maurya, et al., discloses a pharmaceutical composition comprising *Cryptolepis buchanani* extract for treating immunodeficiencies in animals or human beings.

U.S. Pat. No. 6,413,553 to Bandyopadhyay, et al., discloses the preparation of a pharmaceutical composition comprising an effective amount of lyophilised extracts of *Piper betel* and *Murrya koeniggi* as immunomodulator.

U.S. Pat. No. 6,133,440 to Qiu, et al., discloses the preparation and isolation of biologically active polysaccharides from Aloe as immunostimulating, immunomodulating and wound healing activities.

U.S. Pat. No. 6,030,622 to Shehadeh, et al., teaches the preparation of a herbal extract composition comprising Arum, Pomegranate, Tea and Hibiscus for the treatment of immune disorders and HIV infection.

U.S. Pat. No. 5,529,778 to Rohatgi, et al., discloses an ayurvedic formulation comprising *Phyllanthus niruri, Tinospora cordifolia, Phyllanthus emblica, Terminalia belerica* and *Terminalia chebula* etc, for prophylaxis and treatment of AIDS, flu, TB and other immuno-deficiency conditions.

U.S. Pat. No. 6,444,210 to Koumikakis, et al., discloses the effect of bacterial polysaccharides on cell-mediated immunity in animals. This patent further discloses the use of such polysaccharides in preventing and treating various infections as well as in treating carcinomas.

SUMMARY OF THE INVENTION

It is the principal aspect of the present invention to disclose the immunopharmacological effects of the extracts of plant *Symplocos racemosa* and plant *Prosopis glandulosa*.

In another aspect, the present invention discloses the efficacy of the extracts of plants *Symplocos racemosa* and *Prosopis glandulosa* as immunostimulator.

In still another aspect, the present invention provides for a pharmaceutical composition containing a therapeutically effective amount of extracts of plants *Symplocos racemosa* and *Prosopis glandulosa*.

In yet another aspect, the present invention provides for a pharmaceutical composition containing a therapeutically effective amount of extracts of plants *Symplocos racemosa* and *Prosopis glandulosa* or a pharmaceutical composition comprising said extract of said plants, in a pharmaceutically acceptable carrier or otherwise.

In one another aspect, the present invention provides for determining the role of a therapeutically effective amount of extracts of plants *Symplocos racemosa* and *Prosopis glandulosa* in cell mediated immune response.

In still another aspect, the present invention provides for determining the role of a therapeutically effective amount of extracts of plants *Symplocos racemosa* and *Prosopis glandulosa* in humoral antibody response.

In yet another aspect, the present invention discloses methods of treating immunodeficient patients.

It is also an aspect of the present invention to develop a method of treating immunological disorders including AIDS, Hepatitis and Cancer.

In one another aspect, the present invention discloses methods of producing extracts from plant *Symplocos racemosa* and plant *Prosopis glandulosa*.

In one preferred embodiment, there is provided a natural immunostimulant composition comprising a therapeutically effective amount of the extract of plant *Symplocos racemosa* and plant *Prosopis glandulosa*, wherein the extract is prepared by all parts of said herb *Prosopis glandulosa* and preferably its leaves.

In another preferred embodiment, there is provided a natural immunostimulant composition comprising a therapeutically effective amount of the extract of plants *Symplocos racemosa* and *Prosopis glandulosa*, wherein the extract is prepared by all parts of said herb *Symplocos racemosa* and preferably its bark.

In one another preferred embodiment, there is provided a natural immunostimulant composition comprising an aqueous extract of the equimolar mixture of coarse powders of leaves of plant *Prosopis glandulosa* and bark of plant *Symplocos racemosa*.

In yet another preferred embodiment, there is provided a natural immunostimulant composition comprising a therapeutically effective amount of extracts of plants *Symplocos* racemosa and *Prosopis glandulosa* comprising Alkaloids, Bitters, Glycosidic compounds, Tannins, Lipids, Polysaccharides, Flavonoids and Terpenoid glycosides as active constituents.

In one another preferred embodiment, there is provided a method of obtaining the active fraction of extracts of plants *Symplocos racemosa* and *Prosopis glandulosa* by subjecting the extract to bioassay-guided fractionation employing methanol soluble fraction, methanol and water (90:10) soluble fraction, methanol and water (75:25) soluble fraction, methanol and water (50:50) soluble fraction, methanol and water (25:75) soluble fraction and water-soluble fraction.

In still another preferred embodiment, there is provided a method of obtaining the active fraction of extracts of plants *Symplocos racemosa* and *Prosopis glandulosa* by subjecting the extract to bioassay-guided fractionation employing methanol soluble fraction and methanol:water (90:10) fraction.

In yet another preferred embodiment, there is provided a natural immunostimulant composition containing a therapeutically effective amount of extracts of plants *Symplocos racemosa* and *Prosopis glandulosa* in a pharmaceutically acceptable carrier wherein the composition is in an oral dosage form.

In another preferred embodiment, there is provided a natural immunostimulant composition containing a therapeutically effective amount of extracts of plants *Symplocos racemosa* and *Prosopis glandulosa* in an amount of 50 mg to 500 mg and pharmaceutically acceptable carriers comprising sucrose (3.4 to 3.75 gm), Citric acid (0.01 to 0.02 mg), Methyl paraben sodium (0.01 mg), Propyl paraben sodium (0.0025 mg), Strawberry flavor (0.005 mg) and demineralised Water in a quantity sufficient to make up the formulation (Qs) to 5 ml of dosage form.

In yet another preferred embodiment, there is provided a natural immunostimulant composition comprising making granules containing a therapeutically effective amount of extracts of plants *Symplocos racemosa* and *Prosopis glandulosa* in an amount of 50 to 500 mg and pharmaceutically acceptable carriers comprising Microcrystalline cellulose (100 to 450 mg), pregelatinised Starch (about 50 mg), Lactose (50 to 300 mg), Dibasic calcium phosphate (50 to 250 mg), demineralised Water (DM) in a quantity sufficient to make up the formulation (Qs) to 300 to 900 mg of dosage form.

In another preferred embodiment, there is provided a natural pharmaceutical composition comprising granules (500 to 900 mg) as per paragraph [0029] and pharmaceutically acceptable excipients comprising Sodium starch glycolate (about 30 mg), Calcium carbonate (about 14 mg), collodial silicon dioxide (about 3 mg) and Magnesium stearate (about 3 mg) for further compression to obtain tablets.

In another preferred embodiment, there is provided a natural pharmaceutical composition comprising granules (300 to 500 mg) as per paragraph [0029] and pharmaceutically acceptable excipients comprising collodial silicon dioxide (about 2 mg) and Magnesium stearate (about 3 mg) for further filling in capsules.

In one another preferred embodiment, there is provided a delivery system containing natural immunostimulant composition wherein the delivery system comprises tablets, capsules, pills, granules and syrups, powders, concentrates, dry syrups etc.

In yet another preferred embodiment, there is provided a natural immunostimulant composition comprising a potency equivalent of the extract ranging from about 5 mg to about 500 mg.

In a still preferred embodiment, there is provided a method of treating immunodeficiencies by administering to a patient a natural immunostimulant composition comprising a therapeutically effective amount of extracts of plants *Symplocos racemosa* and *Prosopis glandulosa* in a pharmaceutically acceptable carrier or otherwise.

In still another preferred embodiment, there is provided a natural immunostimulant composition, wherein the composition is used for stimulating both specific and non-specific immune reaction, enhancing responsiveness of macrophages and subsets of T-lymphocytes and B-lymphocytes involved in antibody synthesis, stimulating humoral response, enhancing 4 fold (1:256) increases in the primary antibody titre, increasing by 60% in phagocytosis, stimulating proinflammatory cytokines IL-6 at the rate of 1.4 times and TNF-α at the rate of 1.6 times in mouse macrophage and fibroblast cell lines, suppressing inhibitory cytokines IL-10 in mice, treatment of AIDS patients, treatment of all types of cancers, treatment of Hepatitis and relapse conditions.

In still another preferred embodiment, there is provided a process for obtaining a natural immunostimulant composition, the process comprising extracting *Prosopis glandulosa* leaves by percolation, filtering the plant extract, concentrating the plant extract to dryness on rotatory evaporator or on steam bath at optimum temperature and producing a herbal composition comprising the said dry extract and pharmaceutically acceptable carrier.

In still another preferred embodiment of the present invention, there is provided a process for preparation of a novel herbal composition. The method comprising, extracting plant extract from *Prosopis glandulosa* by hot soxhalation, filtering the plant extract, concentrating the plant extract to dryness on rotatory evaporator or on steam bath at optimum temperature and producing a herbal composition employing the said dry extract and pharmaceutically acceptable carrier.

In still another preferred embodiment of the present invention, there is provided a process for preparation of a novel herbal composition. The method comprising extracting plant extract from *Symplocos racemosa* by percolation, filtering the plant extract, concentrating the plant extract to dryness on rotatory evaporator or on steam bath at optimum temperature and producing a herbal composition employing the said dry extract and pharmaceutically acceptable carrier.

In still another preferred embodiment of the present invention, there is provided a process for preparation of a novel herbal composition. The method comprising extracting plant extract from *Symplocos racemosa* by hot soxhalation, filtering the plant extract, concentrating the plant extract to dryness on rotatory evaporator or on steam bath at optimum temperature and producing a herbal composition employing the said dry extract and pharmaceutically acceptable carrier.

BRIEF DESCRIPTION OF THE DRAWINGS

Further objects of the present invention together with additional features contributing thereto and advantages accruing therefrom will be apparent from the description of preferred embodiments of the present invention which are shown in the accompanying drawing figures.

DETAILED DESCRIPTION OF THE INVENTION

Figure 1:
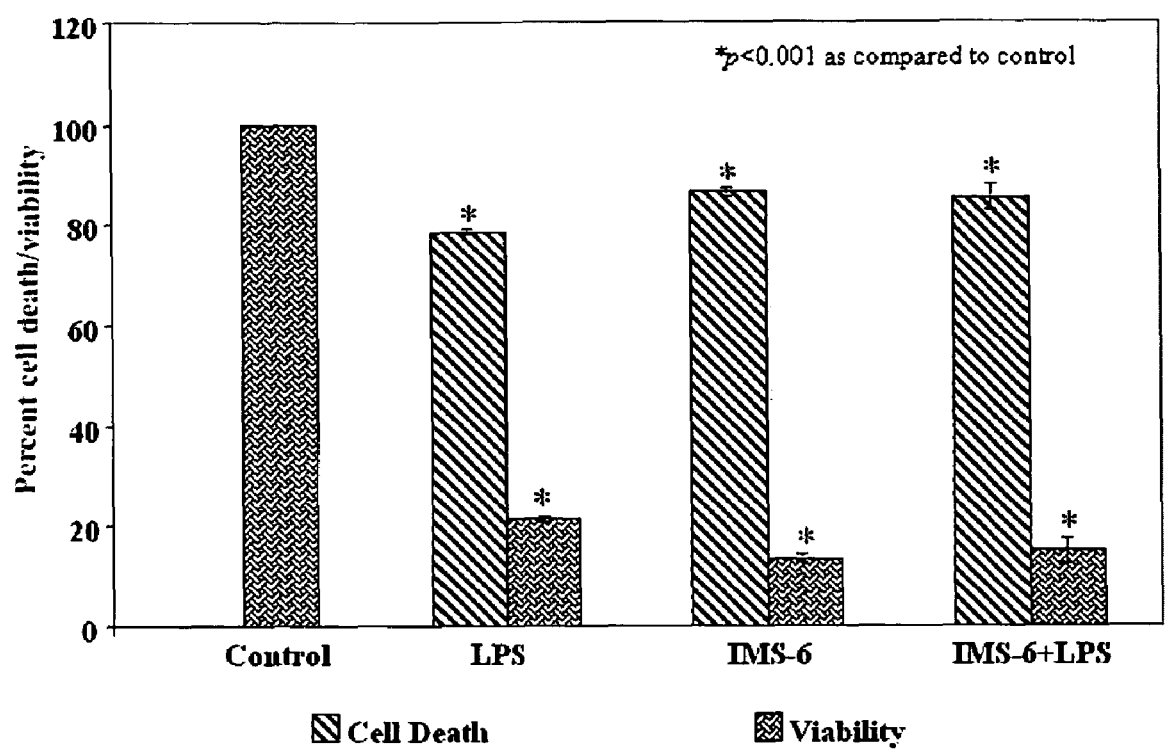
FIG. 1 is a bar graph representation of the immunostimulant property of IMS-6.

The present invention involves the selection and identification of the herbs and obtaining the extract by subjecting the same to solvent extraction. The bioassay guided fractionation of the extract to identify the active markers or active fraction and to develop effective and safe composition for the use in human beings and animals in immunological disorders as an immunostimulant.

*Symplocos racemosa*, Roxb, is an evergreen tree or shrub, 6-8.5 m. tall, seen in abundance in the plains and lower hills throughout North and East India (Chopra, Nayar & Chopra, *Glossary Indian Medicinal Plants,* Publications and Information Directorate, CSIR, New Delhi, 1956, P. 237). The astringent bark of this plant is given for the treatment of diarrhoea & dysentery, liver complaints and dropsy. It is also used in ophthalmia & conjunctivitis. A decoction of the bark is used to stop bleeding of gums. Bark of this plant is also used for the treatment of menorrhagia and other uterine disorders (Sirsi, Indian J. Pharm. 1964, 26, 129; Duthie, 11,20; Haines, IV, 521; Dutta & Basu, J. Instn. Chem India, 1968, 40, 219; I.P.C. 233; Kirt. & Basu, II, 1511; Dastur, Medicinal Plants, 233.)

Symposide, a new flavan glycoside, which showed antifibrinolytic activity was isolated from the bark of *S. racemosa* (Indian J. Chem, 1989, 28B, 982.). A new phenolic glycoside named as benzoylsalireposide and known phenol glycoside, salireposide have been isolated from the bark of *S. racemosa*. These glycosides are reported to show inhibitory activity against snake venom Phosphodiesterase type I (Ahmad et al. Phytochemistry, 2003, 63(2), 217-20.

*Prosopis glandulosa,* Torr, a large shrub or small tree is widely distributed in the arid parts of the tropical and subtropical regions of the world and widely distributed in India (J. K. Maheshwari, *The flora of Delhi,* CSIR, New Delhi, 1963. P.145). The leaves of the genus *Prosopis* are rich in nutrients, especially nitrogen and useful as green manure. Aqueous and alcoholic extract of fresh leaves showed a marked anti bacterial activity against micrococcus pyogenes and basillus coli. (The Wealth of India, Raw materials, Vol. VIII, PID, CSIR, New Delhi,1963, P. 245)

Juliprosopine, an alkaloid exhibiting antibacterial activity was isolated from the leaves of *P. glandulosa* (J. Chem. Soc., Pakistan, 1982, 4, 285; Chem Abstr. 1983, 98, 122848b). Prosopol, Prosopenol and oleanolic acid were reported from the flowers of *P. glandulosa* (Fitoterapia, 1986, 57, 457).

EXAMPLE 1

Preparation of Extract from *Prosopis glandulosa* by Percolation Method:

The shade dried material of leaves of *Prosopis glandulosa* was pulverized to coarse powder and about 1 Kg each of powdered material placed in different flasks and extracted with n-hexane, dichloromethane, chloroform, ethyl acetate, acetone, ethyl alcohol, methanol, water, chloroform and methanol (1:1), methanol and water (1:1) and ethyl alcohol and water (1:1) at room temperature for 24 h to 48 h., then plant extracts were filtered and concentrated to dryness on rotatory evaporator or on steam bath at optimum temperature and under reduced pressure.

EXAMPLE 2

Preparation of Extract from *Prosopis glandulosa* by Hot-soxhalation Method:

The coarse powdered material of leaves of *Prosopis glandulosa* was subjected to hot-soxhalation using solvents n-hexane, dichloromethane, chloroform, ethyl acetate, acetone, ethyl alcohol, methanol, water, chloroform and methanol (1:1), methanol and water (1:1) and ethyl alcohol and water (1:1) at optimum temperature and recycled until extraction is completed, then plant extracts were filtered and concentrated to dryness on rotatory evaporator or on steam bath at optimum temperature.

All extracts such as n-hexane extract (PG-1), dichloromethane extract (PG-2), chloroform extract (PG-3), ethyl acetate extract (PG-4), acetone extract (PG-5), ethyl alcohol extract (PG-6), methanol extract (PG-7), water extract (PG-8), chloroform:methanol (1:1) extract (PG-9), methanol:water (1:1) extract (PG-10) and ethyl alcohol:water (1:1) extract (PG-1) prepared from the leaves of *Prosopis glandulosa* by using percolation method or hot-soxhalation method were subjected to HPTLC (High Performance Thin Layer Chromatography) and HPLC (High performance Liquid chromatography) in various mobile phases on precoated TLC plates (Merck) and ODS column for qualitative and quantitative estimation of marker compounds and active principles. It was found that the extracts PG-1 to PG-11 were qualitatively and quantitatively similar to each other.

EXAMPLE 3

Preparation of Extract from *Symplocos racemosa* by Percolation Method:

The shade dried material of bark of *Symplocos racemosa* were pulverized to coarse powder and about 1 Kg of powdered material was placed in different flasks and extracted with n-hexane, dichloromethane, chloroform, ethyl acetate, acetone, ethyl alcohol, methanol, water, chloroform and methanol (1:1), methanol and water (1:1) and ethyl alcohol and water (1:1) at room temperature for 24 h to 48 h, then plant extract were filtered and concentrated the filtered plant extract to dryness on rotatory evaporator or on steam bath at optimum temperature and under reduced pressure.

EXAMPLE 4

Preparation of Extract from *Symplocos racemosa* by Hot-soxhalation Method:

The coarse powdered material of bark of *Symplocos racemosa* was subjected to hot-soxhalation using solvents n-hexane, dichloromethane, chloroform, ethyl acetate, acetone, ethyl alcohol, methanol, water, chloroform and methanol (1:1), methanol and water (1:1) and ethyl alcohol and water (1:1) at optimum temperature and recycled until extraction is completed, then plant extract were filtered and concentrated the filtered plant extract to dryness on rotatory evaporator or on steam bath at optimum temperature.

All extracts such as n-hexane extract (SR-1), dichloromethane extract (SR-2), chloroform extract (SR-3), ethyl acetate extract (SR-4), acetone extract (SR-5), ethyl alcohol extract (SR-6), methanol extract (SR-7), water extract (SR- 8), chloroform:methanol (1:1) extract (SR-9), methanol:water (1:1) extract (SR-10) and ethyl alcohol:water (1:1) extract (SR-11) prepared from the bark of *Symplocos racemosa* by using percolation method or hot-soxhalation method were subjected to HPTLC (High Performance Thin Layer Chromatography) and HPLC (High performance Liquid chromatography) in various mobile phases on precoated TLC plates (Merck) and ODS column for qualitative and quantitative estimation of marker compounds and active principles. It was found that the extracts SR-1 to SR-11 were qualitatively and quantitatively similar to each other.

Screening of Plant Extracts for Immunomodulatory Activity:

The extracts PG-1 to PG-11 and SR-1 to SR-11 were subjected to biological screening in Mouse macrophage (RAW 264.7) cell and fibroblast (L929) cells for invitro immunomodulatory activity. Following the treatment with sub toxic levels of the extract the percent death in the ACD sensitised cells was taken as end point.

The stock solution of the plant extract was prepared in specified solvent at a concentration of 50 mg/ml. The working concentration of 10 mg/ml solution was prepared in incomplete Dulbecco's Modified Eagle's Medium (DMEM) and filter sterilized for further use in the assays.

Mouse macrophage (RAW 264.7) cells and fibroblast (L929) cells were used in the in vitro assays. These were maintained in DMEM supplemented with 10% fetal calf serum (FCS) at 37° C. in a humidified atmosphere containing 5% $CO_2$/95% air. The cells were sub cultured upon confluence.

EXAMPLE 5

Assay for Immunostimulatory Effects:

Mouse macrophage (RAW 264.7) cells were plated at a cell density of $1\times10^5$ cells/well in a 96 well micro titer plate. After 24 h of incubation they were treated with filtered extract (200 µg/ml), Lipopolysaccharide (1 µg/ml) or media alone and incubated for a further period of 18-24 h. The supernatants as such or diluted ($1/10^{th}$ or $1/20^{th}$) were transferred to pre-incubated (24 h) L929 cells ($4\times105^4$ cells per well). Prior to addition of the supernatant the cells were sensitized with 50 µl of Actinomycin-D (0.33% prepared in DMEM). After 24 h of incubation, 20 µl of MTT (5 mg/ml) and 4 hour later 100 µl of SDS (10%) were added to dissolve the Formazan granules to estimate the cell viability following the transfer of supernatant from the RAW cells. The viability of RAW 264.7 cells (an indicator of extract toxicity) was estimated by adding MTT after the transfer of its supernatant to L929 cells.

EXAMPLE 6

Nitric Oxide (NO) Estimation:

Macrophages are part of immune system (innate immunity) which phagocytose the intruder organism and kill them by release of toxic Nitric Oxide (NO). In this experiment, the ability of the plant extract to stimulate the macrophages for NO production was measured as nitrite released from mouse macrophage cells. Mouse macrophage cells were plated in 96-well culture plates ($1\times10^5$ cells/well) and incubated for 24 h at 37° C. in a humidified atmosphere containing 5% $CO_2$/95% air. The spent media from each well was aspirated and replenished with fresh media and further incubated for 48 h with desired concentration of extract in presence or in absence of Lipopolysaccharide (LPS 1 µg/ml). NO production in the supernatant was measured by micro plate assay. Cell supernatant was mixed with an equal volume of the Griess reagent (1% sulfanilaminde and 0.1% N-[napthyl] ethylenediamine dihydrochloride in 2.5% $H_3PO_4$) at room temperature for 10 min. The absorbance at 540 nm was determined in a microtiter plate reader (Anthos HT II). NO estimation was carried out using standard curve plotted against known quantity of sodium nitroprusside. Results presented are in µM concentration obtained from mean OD of triplicate wells of each group.

EXAMPLE 7

Estimation of IL-6 and TNF-∝ Production:

This experiment was carried out to know whether the plant extract has stimulatory effects on the production of proinflammatory cytokines. Mouse macrophage cells, RAW 264.7 were cultured for 48 hours in the presence or in the absence of filtered plant extract. LPS was used as stimulant for proinflammatory cytokines TNF-∝ and IL-6. Supernatant of these samples were harvested immediately for estimations of TNF-∝ and IL-6 by an ELISA as per the manufacturer's protocol and recorded the results as concentrations in pg/ml.

Invivo Studies:

Wistar rats/Balb/c mice of either sex were used for the study. The animals were housed in standard laboratory conditions and provided with a temperature of 22±3 degree C., relative humidity of 50-55% and a 12 Hr light/dark cycle. Drinking water and a synthetic pelleted diet (Lipton India Ltd, Mumbai) were supplied ad libitum. All experiments were conducted in strict accordance with NIH guidelines (Guide for the care and use of Laboratory Animals NIH Publication No 86-23, Revised 1985) and under the approval of Institutional ethical committee.

EXAMPLE 8

Effect on Humoral Response and Cytokine Production:

Twenty Four Wistar rats of either sex weighing about 200 g each were randomly grouped into 4 groups of 6 animals each. Animals of group I remained as normal control and received normal saline orally for 14 days. Animals of Group II received IMS-6 (200 mg/Kg body weight) orally for 14 days. Animals of group III were similar to control but received an immunosuppressive agent. Animals of Group IV were administered IMS-6 as above and also received a single dose of Cyclophosphamide (immunosuppressive agent). On the $10^{th}$ day animals of all groups were challenged with sheep RBC (SRBC. $5\times10^8$ cells/animal) intra peritonially (ip). On the $12^{th}$ day animals of group III and group IV received Cyclophosphamide (400 mg/Kg per body weight) intra peritonially (ip). On day 14, blood was collected from these groups by orbital route and haemagglunation titer (Antibody levels) in the serum was then established by titration against the SRBC. TNF-∝, IL-2 and IL10 levels were also estimated to understand the proinflammatory and inhibitory cytokines secreted following the treatment with plant extract.

a. Levels of Immunoglobulin:

For this purpose, serum samples collected from Wistar rats (both treatment and control groups) were serially diluted using 0.1% BSA prepared in normal saline in a 96 well "V" bottom plate and were treated with an equal volume of 0.1 SRBC (washed at least 3 times to remove the Alsavor's residues). Highest dilution of the serum indicating agglutination of the SRBC was taken as the endpoint for assessing the levels of SRBC specific immunoglobulin present in the serum b. Levels of Cytokines:

The levels of TNF-α, IL-4 and IL-6 in the serum collected from the animals treated with extract orally (200 mg/kg) for 14 days were measured by an ELISA system as per the manufacture's protocol. The results were expressed as concentration in pg/ml both in control and the treated groups.

EXAMPLE 9

*E. coli* Induced Abdominal Sepsis:

This experiment was conducted in Balb/c mice treated with plant extract at 200 mg/kg body weight orally for 14 days. The treated and untreated mice were challenged by intra peritoneal administration of $5 \times 10^8$ cells per ml of pathogenic *E. coli*. The protection offered by the plant extract in the treated group was measured by comparing with the control on the incidence of abdominal sepsis and percent mortality.

EXAMPLE 10

Phagocytic Index (PI):

In this experiment the ability of the macrophages to internalise the foreign particle was assessed in presence or in absence of the plant extract. Alveolar macrophages were collected under sterile precaution from Balb-c mice (of age 4-5 weeks weighing 20 g each) treated with extract orally (200 mg/kg) for 7 days. Macrophages were washed twice with DMEM supplemented with 10% FCS and were seeded in a 96-well microtiter plate at $1 \times 10^6$ cells/well and incubated for 24 h at 37° C. in a humidified atmosphere containing 5% $CO_2$/95% air. The cultured macrophages were then incubated with the heat killed *Candida albicans* ($10^8$ cells/ml) for a further period of 24 hours. The macrophages were then stained to assess the *Candida albicans* particles present in the cytoplasm of macrophages. Number of macrophages containing the ingested particles from among the first 200 counted was expressed as the Phagocytic index (PI).

Statistical Analysis:

The data were statistically analysed using One Way Analysis of Variance using Bonferroni's Multiple Comparison Test for all parameters except for the *E. coli* induced abdominal sepsis/mortality where the Chi-Square test with Yates correction was adopted. The levels of significance were expressed at $p<0.05$ to $p<0.001$ levels as per the result of each analysis.

The list of extracts screened and their invitro immunomodulatory results are summarised in Tables 1 & 2.

TABLE 1

| Plant extract | Proinflammatory Cytokine death (%) | NO (μM) |
|---|---|---|
| Control | 0.00 | 753.50 ± 3.5 |
| PG-1 | 26.88 | 721.00 ± 22.0 |
| PG-2 | 26.95 | 745.00 ± 10.5 |
| PG-3 | 26.64 | 751.00 ± 38.0 |
| PG-4 | 36.29 | 748.50 ± 34.5 |
| PG-5 | 36.85 | 743.50 ± 0.5 |
| PG-6 | 18.90 | 716.50 ± 26.5 |
| PG-7 | 5.09 | 843.00 ± 2.0 |
| PG-8 | 61.25 | 1223.00 ± 29.0* |
| PG-9 | 18.25 | 752.00 ± 1.5 |
| PG-10 | 53.30 | 871.50 ± 26.50 |
| PG-11 | 33.30 | 760.50 ± 2.5 |

*$P < 0.001$ as compared to control.
Values are expressed as mean ± SEM (n = 2).

TABLE 2

| Plant extract | Proinflammatory Cytokine death (%) | NO (μM) |
|---|---|---|
| Control | 0.00 | 753.50 ± 3.5 |
| SR-1 | 19.10 | 707.00 ± 15.5 |
| SR-2 | 15.20 | 736.00 ± 5.00 |
| SR-3 | 20.10 | 749.00 ± 9.0 |
| SR-4 | 58.50 | 698.00 ± 44.5 |
| SR-5 | 40.10 | 751.00 ± 3.0 |
| SR-6 | 20.20 | 546.50 ± 21.5 |
| SR-7 | 16.10 | 748.00 ± 108.0 |
| SR-8 | 67.30 | 788.00 ± 11.0 |
| SR-9 | 57.90 | 745.00 ± 3.5 |
| SR-10 | 66.70 | 652.00 ± 1.5 |
| SR-11 | 14.30 | 648.00 ± 28.0 |

P values are not significant as compared to control.
Values are expressed as mean ± SEM (n = 2)

The above invitro results demonstrate the immunomodulatory activity of extracts PG-8 and SR-8 more potent than the other extracts and also devoid of any toxicity. These two short listed extracts viz. PG-8 and SR-8 were selected for further study of immunostimulatory activity. As the objective of the present invention is to formulate a natural immunostimulant composition, which is effective and free of undesirable side effects, the various combinations of these extracts were prepared and subjected to invitro immunostimulatory activities for potent combination of herbal composition for immunostimulatory activity. The various combinations of the extracts PG-8 and SR-8 were prepared in the ratio of PG-8:SR-8 (1:9) extract (IMS-1), PG-8:SR-8 (9:1) extract (IMS-2), PG-8:SR-8 (1:3) extract (IMS-3), PG-8:SR-8 (3:1) extract (IMS-4), PG-8:SR-8 (1:4) extract (IMS-5), PG-8:SR-8 (1:1) extract (IMS-6) and PG-8:SR-8 (4:1) extract (IMS-7).

The in vitro immunomodulatory activity results of various combinations of PG-8 and SR-8 are shown in Table 3

TABLE 3

| Extract | Proinflammatory Cytokine death (%) | NO (μM) |
|---|---|---|
| Control | 0.00 | 753.50 ± 3.5 |
| IMS-1 | 78.17 | 846.10 ± 15.3 |
| IMS-2 | 78.17 | 798.07 ± 48.0 |
| IMS-3 | 82.00 | 1129.27 ± 21.0* |
| IMS-4 | 76.00 | 943.00 ± 71.80 |
| IMS-5 | 84.60 | 946.15 ± 53.80 |
| IMS-6 | 88.00 | 1301.28 ± 91.0** |
| IMS-7 | 85.00 | 784.60 ± 46.15 |

**$P < 0.01$ as compared to control.
*$P < 0.05$ as compared to control.
Values are expressed as mean ± SEM (n = 2)

The above table demonstrates the combination extract IMS-6 has high stimulation ability of proinflammatory cytokines from the macrophages, ability to stimulate the production of significant levels of NO and moderate to high level stimulation of the innate and acquired immunity and absolutely safe without any undesirable side effects.

Immunostimulatory Effects of IMS-6:

In the present study, Immunostimulatory effects of plant extract IMS-6, to produce proinflammatory cytokines TNF-α and IL-6 were assessed. In vitro study was conducted in mouse macrophage cells (RAW 264.7) and in fibroblast cells (L929). The levels of macrophage activation (phagocytic activity), cell mediated and humoral responses were some of the other parameters investigated to assess the immunostimulatory effects of the product. In vivo and ex-vivo studies were also conducted to assess the levels of cytokines produced in response to the plant extract treatment.

Assay for Immunostimulatory Effects:

The assay conducted in the cell lines indicated that the supernatant of the macrophage cells were able to successfully cause more than 50% death in the ACD sensitized L929 cells (end point) comparable to the levels in LPS group. The control group however did not exhibit the same levels of damage. Further, MTT reduction assay indicated that the plant extract by itself was not toxic to the cells. The significantly higher levels of the death in L929 cells ($p<0.001$) in the IMS-6 treated group compared to control following the transfer of supernatant from RAW cells was not on account of IMS-6 toxicity but due the cytokines released from the activated macrophages. Correspondingly the treatment group showed significantly lower levels ($p<0.001$) of survival compared to control. The higher levels of death in L929 cells indicate that IMS-6 was able to stimulate the macrophage to produce the proinflammatory cytokines. These results are shown in Table 4 and FIG. 1.

TABLE 4

Effect of IMS-6 on Proinflammatory cytokine induced cell death in ACD sensitized L929 cells:

| Treatment Group | Proinflammatory Cytokine induced Cell Death (%) |
|---|---|
| Control | 0 |
| LPS | 79.0 |
| IMS-6 | 87.11 |
| IMS-6 + LPS | 87.66 |

Figure 2:
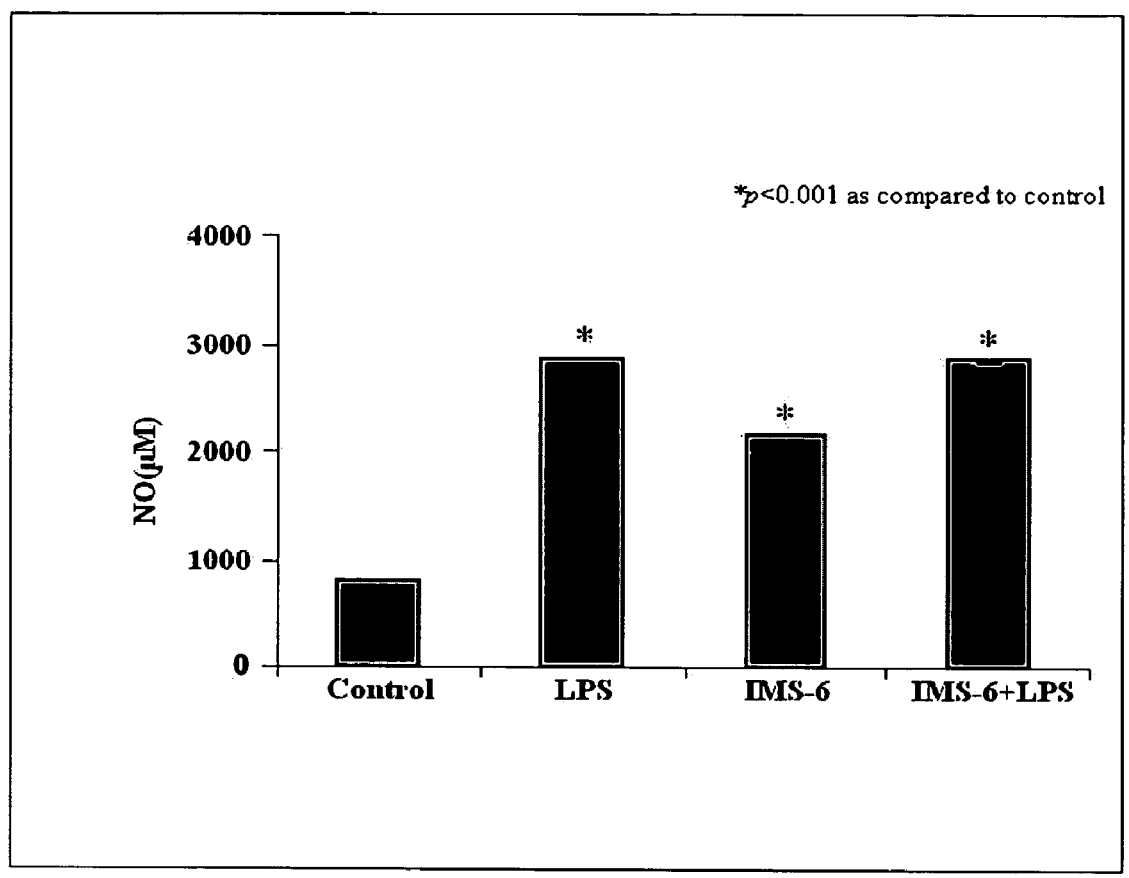
FIG. 2 is a bar graph representation of the effect of IMS-6 on NO production in RAW-264.7 Cells.

Nitric Oxide (NO) Estimation:

This experiment indicated that the macrophages were activated by the plant extract to produce nitric oxide to the levels comparable to LPS group, indicating that the plant extract was able to stimulate the innate immune system of the body and thus help preventing the invading organisms. Results are shown in Table 5 and FIG. 2.

TABLE 5

| Groups | NO Levels (μM) |
|---|---|
| Control | 800 ± 50 |
| LPS | 2862.50 ± 87.50* |
| IMS-6 | 2150.00 ± 50.00* |
| IMS-6 + LPS | 2850.00 ± 50.00* |

* $p < 0.001$ as compared to control

The nitrite release in the IMS-6 treated group (2150±50 μM) was significantly higher ($p<0.001$) compared to control (800±50 μM). The group which received LPS along with the plant extract IMS-6 recorded NO levels of 2850±50 μM and was also significantly higher ($p<0.001$) compared to control.

Figure 3:
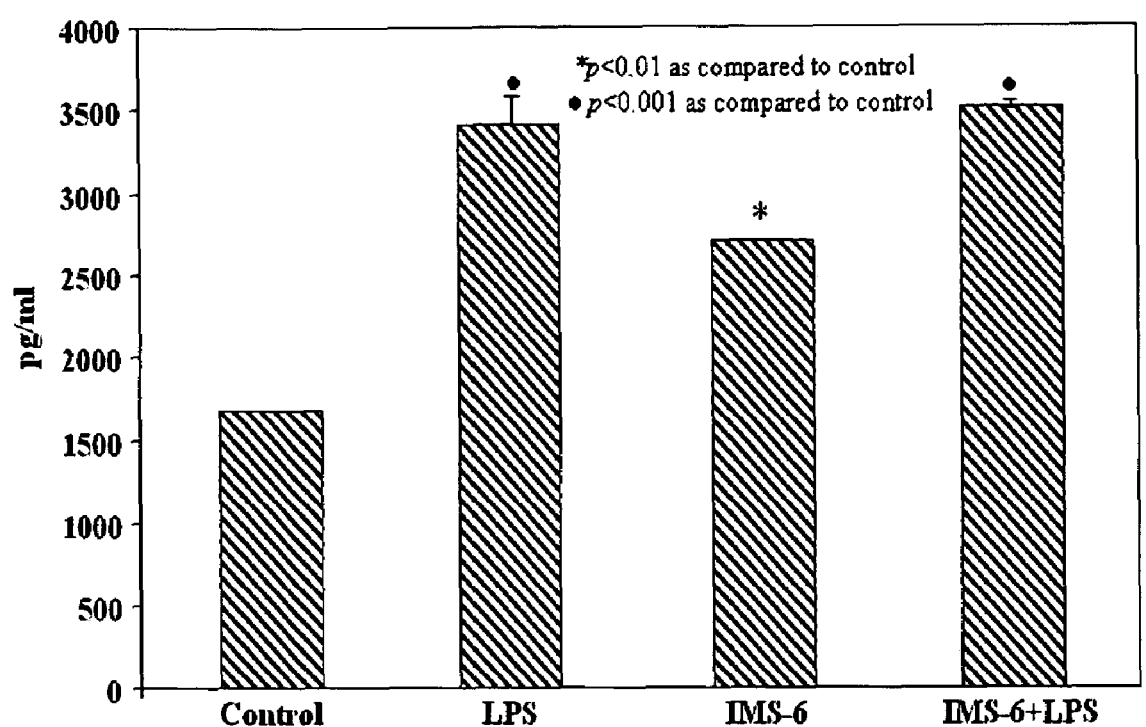
FIG. 3 is a bar graph representation of the effect of IMS-6 on TNF-α production in RAW-264.7 Cells.

Estimation of TNF-α and IL-6 Production:

In vitro cytokine estimation in the supernatant of macrophage cells indicated high levels of proinflammatory cytokines in the IMS 6 treated group compared to the control. The levels of TNF-α were significantly higher ($p<0.01$) in the IMS 6 treated groups compared to the control. Further, the TNF-α levels were significantly higher ($p<0.001$) in the IMS 6 and LPS combination group indicating the synergistic effect on account of IMS 6. Treatment of RAW cells with the IMS 6 for 24 produced an increase in the levels of unbound TNF-α (2703.00±3.70 pg/ml) compared to control (1662.00±3.50 pg/ml). The levels in groups treated with IMS-6 and LPS also showed a substantial increase (3516.00±24.50 pg/ml) compared group treated with LPS alone (3432.00±140.50 pg/ml). Results are shown in Table-6 and FIG. 3.

TABLE 6

| Groups | TNF α Levels (pg/ml) |
|---|---|
| Control | 1662.00 ± 3.50 |
| LPS | 3432.00 ± 140.50˙ |
| IMS 6 | 2703.00 ± 3.70* |
| IMS6 + LPS | 3516.00 ± 24.50˙ |

Figure 4:
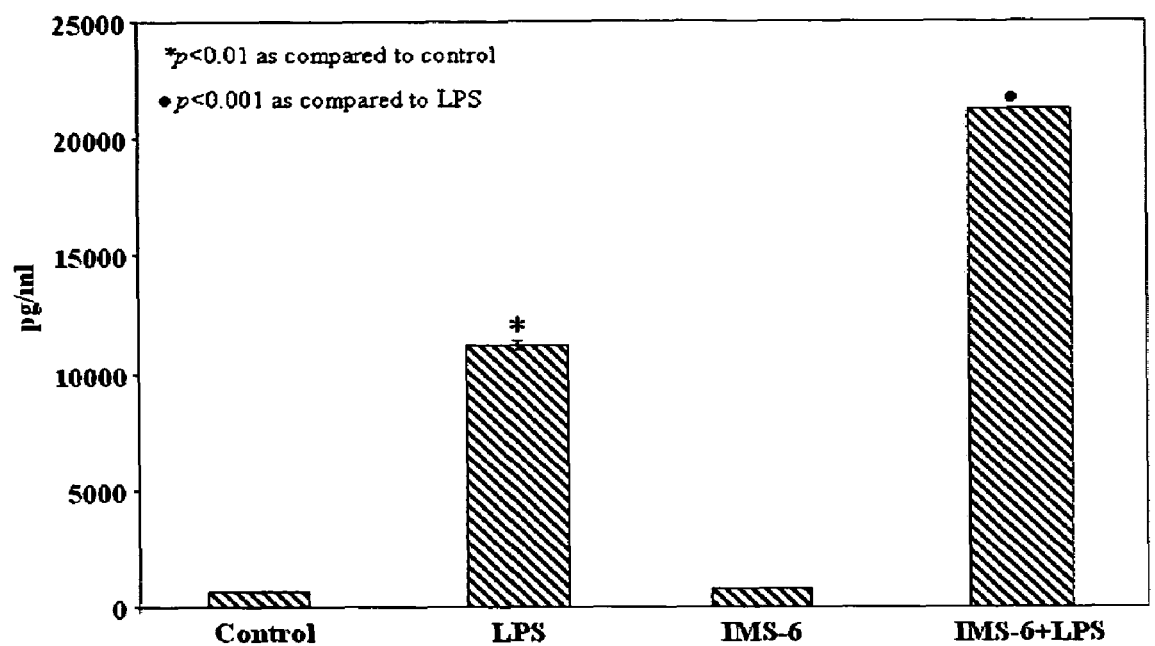
FIG. 4 is a bar graph representation of the effect of IMS-6 on IL-6 production in RAW-264.7 Cells.

The levels of IL-6 in the IMS-6 groups were higher than the control and exhibited the synergistic effect in the group treated with IMS-6 along with LPS and was significantly higher ($p<0.001$) compared to the groups treated with LPS alone. Results are shown in Table 7 and FIG. 4.

TABLE 7

| Groups | IL-6 Conc. (pg/ml) |
|---|---|
| Control | 542 ± 4 |
| LPS* | 11187 ± 214 |
| IMS-6 | 760 ± 6.8 |
| IMS-6 + LPS | 21254 ± 10.4 |

Figure 5:
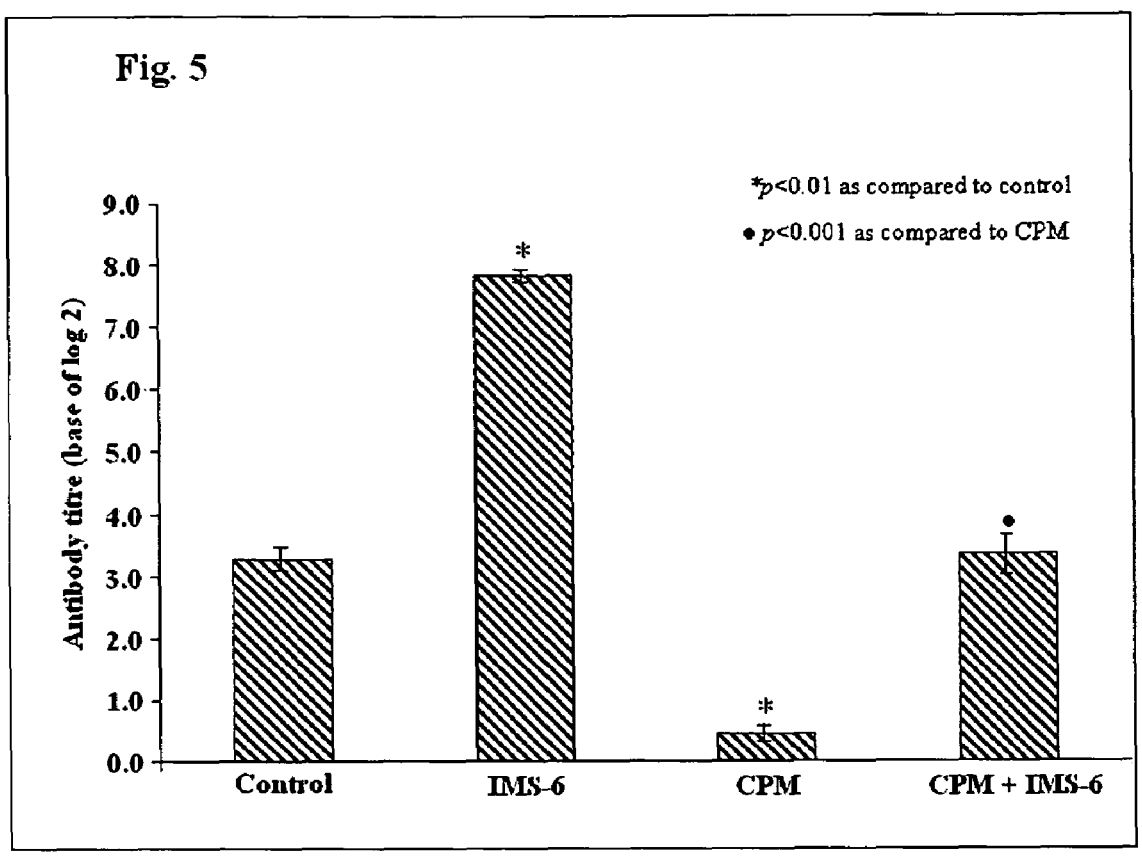
FIG. 5 is a bar graph representation of the effect of IMS-6 on humoral response in normal and immunocompromised rats.

Effect on Humoral Response and Cytokine Production:

Wistar rats treated with the IMS-6 showed significantly higher hemagglutination titer (HA) ($p<0.01$) compared to control where the mean values stood at 3.278±0.181 only. The group of animals challenged with SRBC and subsequently with the cyclophosphamide did not elicit any immune response and had significantly lower ($p<0.01$) antibody titer compared to control animals. The immune suppressant activity of the cyclophosphamide was completely overcome in the animals treated simultaneously with IMS6 where the antibody response stood at significantly higher levels ($p<0.001$) compared to the Cyclophosphamide group indicating that IMS-6 was able to restore the HA titer in immune suppressed animals. Results are shown in Table 8 and FIG. 5.

TABLE 8

| Groups | Antibody titre |
|---|---|
| Control | 3.278 ± 0.181 |
| IMS-6 | 7.833 ± 0.114* |
| Cyclophosphamide | 0.444 ± 0.141* |
| Cyclophosphamide + IMS-6 | 3.333 ± 0.31˙ |

Error bar represents the mean ± SEM of mean values of three experiments where *$P < 0.01$ as compared to control and ˙$p < 0.001$ as compared to cyclophosphamide.

Figure 6:
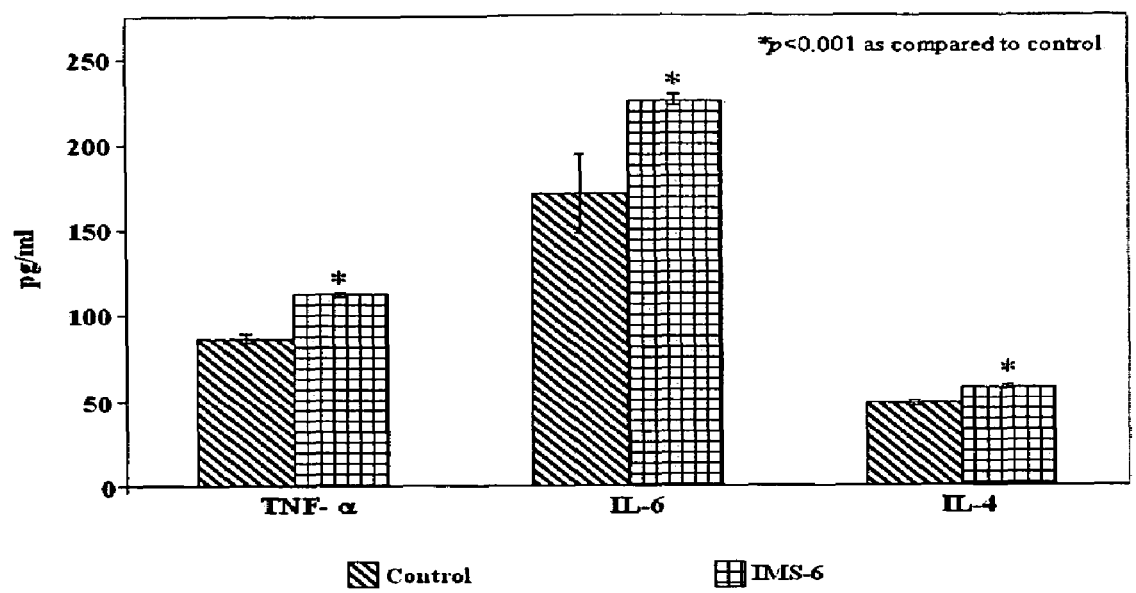
FIG. 6 is a bar graph representing the effect of IMS-6 on serum cytokine levels in rats.

Levels of Cytokines:

The studies conducted in Wistar rats indicated that the IMS-6 treated animals had significantly higher levels ($p<0.001$) of proinflammatory cytokines TNF-α, IL-6 and IL-4 compared to the control animals. Further, the levels immunosuppressive cytokine IL-10 was at not detectable range (data not provided) compared to the control group. This result suggests that the plant extract was able to stimulate the immune system to release the proinflammatory responses. Results are shown in Table 9 and FIG. 6.

TABLE 9

| Groups | Control* | IMS-6* |
|---|---|---|
| TNF-α | 87.07 ± 2.72 | 112.92 ± 1.36 |
| IL-6 | 170.65 ± 22.65 | 225.55 ± 3.33 |
| IL-4 | 48.66 ± 1.3 | 58.33 ± 1.66 |

Error bar represents the mean ± SEM of mean values from three different experiments where n = 10.
*Values are in pg/ml
*p < 0.001 as compared to control.

Figure 7:
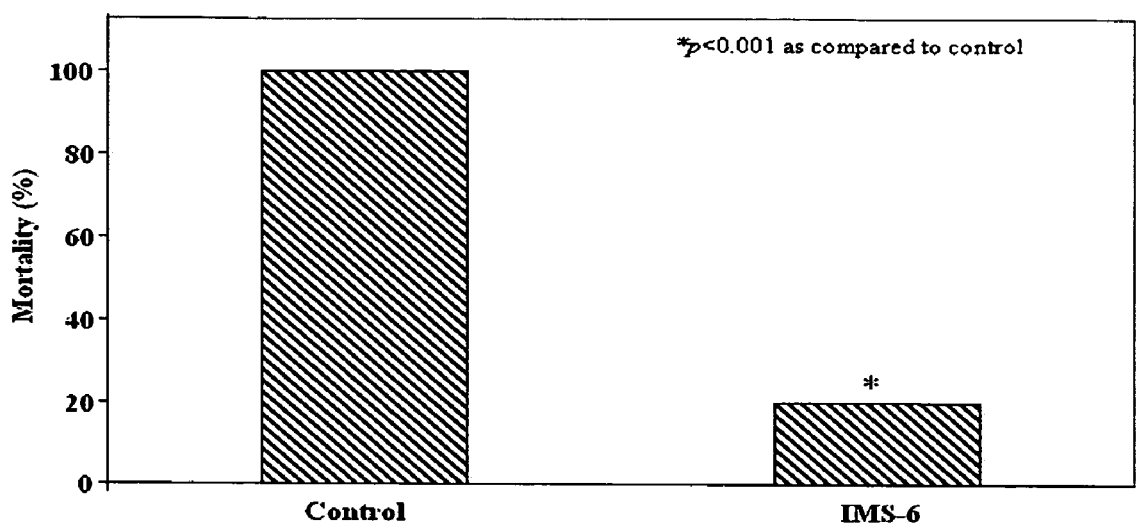
FIG. 7 is a bar graph representing the protective effect of IMS-6 in *E. coli*-induced abdominal species in mice.

*E. coli* Induced Abdominal Sepsis:

The study conducted on the incidence of abdominal sepsis and mortality in the *E. coli* challenged mice treated with IMS-6 showed significantly higher levels of protection (p<0.001) compared to control. While the extent of mortality in the IMS-6 treated group was on 20%, the same in the control was 100% following a 24-hour challenge period. Further the animals treated with IMS-6 were able to survive beyond 5 days suggesting the activation of cell-mediated immunity in this group. The blood samples collected from the animals when cultured on an agar plate showed lower colony count in the IMS-6 treated animals compared to the control animals. Results are shown in FIG. 7.

Figure 8:
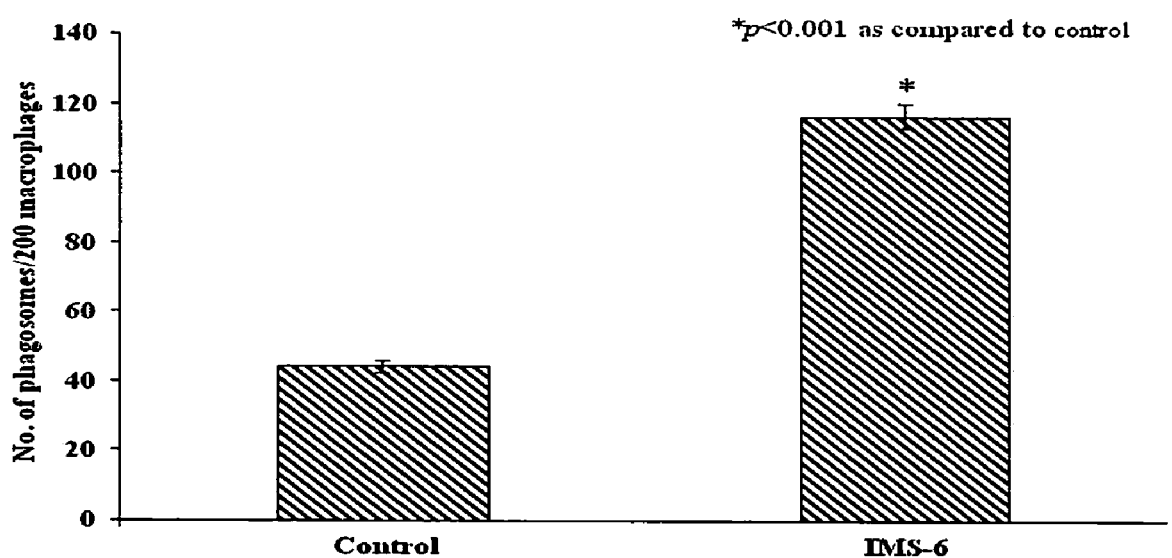
FIG. 8 is a bar graph representing the effect of IMS-6 on phagocytic index in mice.

Phagocytic Index:

Alveolar macrophages collected from IMS-6 treated mice indicated a high degree of protective activation of innate immune system. This was evident due to the enhanced ability of the macrophages to phagocytose the interloper in an ex-vitro experiment detailed earlier. A total of 120 macrophages from out of 200 macrophages counted indicated the presence of the engulfed *Candida albicans* particles in the IMS-6 treated group which was significantly higher (p<0.001) compared to the control wherein only 44 of them showed the active phagocytosis. Results are shown in FIG. 8.

The alveolar macrophages collected from the mice treated with the IMS-6 thus exhibited high efficiency in internalising the *Candida albicans* particles.

EXAMPLE 11

Bioassay Guided Fractionation of Active Extract IMS-6:

About 100 g of the combined extract (IMS-6) is macerated with methanol to give methanol soluble fraction (IMS-6A) and methanol insoluble fraction. The methanol insoluble extract was further fractionated into methanol:water (10%) IMS-6B, methanol:water (25%) IMS-6C, methanol:water (50%) IMS-6D, methanol-water (75%) IMS-6E and water (100%) IMS-6F fractions. All fractions IMS-6A to IMS-6F were shown immunostimulating activity and the results are given in Table 10. The methanol soluble fraction IMS-6A and methanol:water (10%) fraction, IMS-6B have found to be more potent. The methanol soluble fraction was taken up for further detailed study of identification of marker compounds and active principles responsible for immunostimulating activity.

EXAMPLE 12

Column Chromatograhy of IMS-6A:

About 25 g of IMS-6A fraction was subjected to column chromatography over silica gel (60-120 mesh) and eluted with increasing gradient of hexane, hexane and ethyl acetate solvent mixture, ethyl acetate and ethyl acetate and methanol solvent mixture. Twenty two fractions of 250 ml each were collected and mixed after analysing TLC over precoated TLC plates. The semi purified fractions were tested for the presence of Alkaloids, Glycosides, Amino Acids, Amino glycosides, polysaccharides, flavonoids and Tannins. The semi purified fractions IMS-6A1 to IMS-6A12 were subjected to invitro immunomodulatory activity, and results are summarized in Table 11.

TABLE 10

| Fraction | Proinflammatory cytokine death (%) | NO (μM) |
|---|---|---|
| Control | 0.00 | 458.00 ± 3.5 |
| IMS-6A | 88.0 | 874.00 ± 25.0* |
| IMS-6B | 78.0 | 809.00 ± 4.5* |
| IMS-6C | 52.2 | 695.50 ± 45.5** |
| IMS-6D | 47.2 | 732.00 ± 18.0* |
| IMS-6E | 46.5 | 722.00 ± 16.5* |
| IMS-6F | 55.1 | 683.50 ± 24.5** |

*P < 0.001 as compared to control.
**P < 0.01 as compared to control.
Values are expressed as mean ± SEM (n = 2).

TABLE 11

| Fraction | Proinflammatory cytokine death (%) | NO (μM) |
|---|---|---|
| Control | 0.00 | 750.50 ± 0.5 |
| IMS-6A1 | 57.6 | 752.00 ± 2.0 |
| IMS-6A2 | 53.4 | 711.00 ± 1.0 |
| IMS-6A3 | 52.8 | 750.50 ± 0.5 |
| IMS-6A4 | 56.4 | 732.00 ± 20.0 |
| IMS-6A5 | 57.9 | 749.50 ± 4.5 |
| IMS-6A6 | 75.8 | 907.50 ± 7.5* |
| IMS-6A7 | 55.8 | 759.50 ± 0.5 |
| IMS-6A8 | 56.2 | 707.50 ± 7.5 |
| IMS-6A9 | 76.2 | 917.50 ± 17.5* |
| IMS-6A10 | 87.8 | 1325.00 ± 25.0* |
| IMS-6A11 | 50.3 | 763.00 ± 5.0 |
| IMS-6A12 | 57.1 | 752.00 ± 2.0 |

*P < 0.001 as compared to control.

The bioassay guided fractionation and purification of IMS-6 extract demonstrate the bioactivity in IMS-6A and its semi purified fraction IMS-6A10 in addition to all other fractions and its semi purified fractions that have shown moderate to good activity. It is clear from the above two tables that the activity of IMS-6 could be due to the presence of many active compounds which shows synergic action as a whole in IMS-6 extract. It is therefore the present invention is unique and novel for combining in a particular ratio of two herbal extracts which is superior than individual extracts and its fractions.

Process for preparation of Pharmaceutical Formulations comprising extract of plants *Symplocos racemosa* and *Prosopis glandulosa* and pharmaceutically acceptable carriers to provide different delivery systems.

EXAMPLE 13

Preparation of IMS-6 Syrup:

| Sl. No. | Name of Ingredient, | Formula I | Formula II | Formula III | Formula IV | Formula V |
|---|---|---|---|---|---|---|
| 1 | IMS-6 extract IH | 50 mg | 100 mg | 125 mg | 250 mg | 500 mg |
| 2 | Sugar D 30 sucrose/IP | 3.4 gm | 3.4 gm | 3.4 gm | 3.5 gm | 3.75 gm |
| 3 | Citric acid IP | 0.01 mg | 0.01 mg | 0.01 mg | 0.02 mg | 0.02 mg |
| 4 | Methyl paraben sodium IP | 0.01 mg | 0.01 mg | 0.01 mg | 0.01 mg | 0.01 mg |
| 5 | Propyl paraben sodium IP | 0.0025 mg | 0.0025 mg | 0.0025 mg | 0.0025 mg | 0.0025 mg |
| 6 | Strawberry flavor IFF | 0.005 mg | 0.005 mg | 0.005 mg | 0.005 mg | 0.005 mg |
| 7 | DM water (demineralised water) IP | Qs to 5 ml | Qs to 5 ml | Qs to 5 ml | Qs to 5 ml | Qs to 5 ml |

Process for Preparation:

First sugar was dissolved with DM Water in a jacketed vessel, then extract was added into the solution and mixed for 10-15 min. and the resultant was filtered through Polypropylene pad into another jacketed vessel, then citric acid was dissolved in small quantity of DM deminieralised water and mixed with the resultant, methyl paraben sodium and propyl paraben sodium was dissolved in small quantity of DM (demineralised) water and mixed with the resultant mixture at 60° C.-70° C. and then the mixture was cooled, flavor was added at 40° C. or less and mixed for 5-10 min. Then the volume was maintained, and mixed for 10-15 min. and filtered to a clean storage vessel through Polypropylene pad (10 micron).

EXAMPLE 14

Preparation of IMS-6 Tablets:

mass was passed through Sieve No. 8 and dried in suitable drier till the moisture content of 2-4%. The dried mass was passed through Sieve No. 16 and the lot was mixed uniformly.

Formula III: P.G. Starch IP (pregelantinised starch) and Lactose IP (Both passed through Sieve No. 60) were loaded in a suitable mixer and mixed for 5 mins. and granulated with IMS-6 extract IH and DM (demineralised) Water. The wet mass was passed through Sieve No. 8 and dried in suitable drier till the moisture content of 2-4%. The dried mass was passed through Sieve No. 16 and the lot was mixed uniformly.

Formula IV: Lactose IP and Dibasic calcium phosphate IP (Both passed through Sieve No. 60) were loaded in a suitable mixer and mixed for 5 mins. and granulated with IMS-6 extract IH and DM (demineralised) Water. The wet mass was passed through Sieve No. 8 and dried in suitable drier till the moisture content of 2-4%. The dried mass was passed through Sieve No. 16 and the lot was mixed uniformly.

Formula V: Microcrystalline cellulose IP, Lactose IP and Dibasic calcium phosphate IP (Both passed through Sieve No. 60) were loaded in a suitable mixer and mixed for 5 mins.

| Sl No. | Name of Ingredient, | Formula I | Formula II | Formula III | Formula IV | Formula V | Formula VI |
|---|---|---|---|---|---|---|---|
| 1 | IMS-6 extract IH | 50 mg | 100 mg | 150 mg | 200 mg | 250 mg | 500 mg |
| 2 | Microcrystalline cellulose IP | 450 mg | 350 mg | — | — | 100 mg | 100 mg |
| 3 | P.G. Starch (pregelatinised starch) IP | — | 50 mg | 50 mg | — | — | — |
| 4 | Lactose IP | — | — | 300 mg | 50 mg | 100 mg | 150 mg |
| 5 | Dibasic calcium phosphate IP | — | — | — | 250 mg | 50 mg | 200 mg |
| 6 | DM water (demineralised water) IH | Q.S. | Q.S. | Q.S. | Q.S. | Q.S. | Q.S. |

Process for Preparation:

Formula I: Microcrystalline cellulose IP (Passed through Sieve No. 60) was loaded in a suitable mixer and granulated with IMS-6 extract IH and DM (demineralised) Water. The wet mass was passed through Sieve No. 8 and dried in suitable drier till the moisture content of 2-4%. The dried mass was passed through Sieve No. 16 and the lot was mixed uniformly.

Formula II: Microcrystalline cellulose IP and P.G. Starch IP (Both passed through Sieve No. 60) were loaded in a suitable mixer and mixed for 5 mins. and granulated with IMS-6 extract IH and DM (demineralised) Water. The wet and granulated with IMS-6 extract IH and DM (demineralised) Water. The wet mass was passed through Sieve No.8 and dried in suitable drier till the moisture of 2-4%. The dried mass was passed through Sieve No.16 and the lot was mixed uniformly.

Formula VI: Microcrystalline cellulose IP, Lactose IP and Dibasic calcium phosphate IP (Both passed through Sieve No.60) were loaded in a suitable mixer and mixed for 5 mins. and granulated with IMS-6 extract IH and DM (demineralised) Water. The wet mass was passed through Sieve No. 8 and dried in suitable drier till the moisture of 2-4%. The dried mass was passed through Sieve No.16 and the lot was mixed uniformly.

Pharmaceutical Ingredients for Tablet Compression (Formula I to VI)

| Sl. No. | Name of Ingredient | Formula I to V Mg/Tablet | Formula VI Mg/Tablet |
|---|---|---|---|
| 1 | IMS-6 granules IH | 500.00 | 950.00 |
| 2 | Sodium starch Glycolate IP | 30.00 | 30.00 |
| 3 | Calcium carbonate IP | 14.00 | 14.00 |
| 4 | Cabosil M5 (colloidal silicon dioxide) IP/USP | 3.00 | 3.00 |
| 5 | Magnesium stearate IP | 3.00 | 3.00 |
| | Total | 550.00 | 1000.00 |

Procedure of Compression:

Sodium starch Glycolate IP, Calcium carbonate IP and Cabosil M5 (colloidal silicon dioxide)IP/USP were mixed and passed through Sieve No. 60 and blended in a suitable mixer with IMS-6 granules IH for 5 min., Magnesium stearate IP was passed through Sieve No. 60 and blended with the above for 3 min. The blend was ready for tablet compression.

Tooling: Caplet Shape, Round Shape, Oval Shape, and Triangular Shape etc.

EXAMPLE 15

Preparation of IMS-6 Capsules:

| Sl No. | Name of Ingredient, | Formula I | Formula II | Formula III | Formula IV | Formula V |
|---|---|---|---|---|---|---|
| 1 | IMS-6 extract IH | 50 mg | 100 mg | 150 mg | 200 mg | 250 mg |
| 2 | Micro crystalline cellulose IP | 250 mg | 150 mg | — | — | 100 mg |
| 3 | P.G. Starch (pregelatinised starch) IP | — | 50 mg | 50 mg | — | — |
| 4 | Lactose IP | — | — | 300 mg | 50 mg | 100 mg |
| 5 | Dibasic calcium phosphate IP | — | — | — | 250 mg | 50 mg |
| 6 | DM (demineralised) water IH | Q.S. | Q.S | Q.S. | Q.S. | Q.S. |

Process for Preparation:

Formula I: Microcrystalline cellulose IP (Passed through Sieve No.60) was loaded in a suitable mixer and granulated with IMS-6 extract IH and DM (demineralised) Water. The wet mass was passed through Sieve No.8 and dried in suitable drier till the moisture content of 2-4%. The dried mass was passed through Sieve No.16 and the lot was mixed uniformly.

Formula II: Microcrystalline cellulose IP and P. G. Starch IP (Both passed through Sieve No. 60) were loaded in a suitable mixer and mixed for 5 min. and granulated with IMS-6 extract IH and DM (demineralised) Water. The wet mass was passed through Sieve No. 8 and dried in suitable drier till the moisture content of 2-4%. The dried mass was passed through Sieve No.16 and mixed uniformly.

Formula III: P.G. Starch IP and Lactose IP (Both passed through Sieve No. 60) were loaded in a suitable mixer and mixed for 5 min. and granulated with IMS-6 extract IH and DM (demineralised) Water. The wet mass was passed through Sieve No. 8 and dried in suitable drier till the moisture content of 2-4%. The dried mass was passed through Sieve No. 16 and mixed uniformly.

Formula IV: Lactose IP and Dibasic calcium phosphate IP (Both passed through Sieve No. 60) were loaded in a suitable mixer and mixed for 5 min. and granulated with IMS-6 extract IH and DM (demineralised) Water. The wet mass passed through Sieve No. 8 and dried in suitable drier till the moisture content of 2-4%. The dried mass was passed through Sieve No. 16 and mixed uniformly.

Formula V: Microcrystalline cellulose IP, Lactose IP and Dibasic calcium phosphate IP (all passed through Sieve No. 60) were loaded in a suitable mixer and mixed for 5 min. and granulated with IMS-6 extract IH and DM (demineralised) Water. The wet mass was passed through Sieve No. 8 and dried in suitable drier till the moisture content of 2-4%. The dried mass was passed through Sieve No. 16 and mixed uniformly.

Capsule Filling Formula:

| Sl. No. | Name of Ingredient, | Formula I to II Mg/Capsule | Formula III to V Mg/Capsule |
|---|---|---|---|
| 1 | IMS-6 granules IH | 300.00 | 500.00 |
| 2 | Cabosil M5 (colloidal silicon dioxide) IP/USP | 2.00 | 2.00 |
| 3 | Magnesium stearate IP | 3.00 | 3.00 |
| | Total | 305.00 | 505.00 |

Description of capsule: Size '0' and '00' Clear transparent/or colored empty hard gelatine and/or Vegetable (HPMC) capsules.

Immune stimulators are of great value in the treatment of Cancer conditions, Hepatitis B, HI and in other immunity breakdown situations commonly associated with the bacterial and viral diseases.

Anticancer drugs generally inhibit the cell proliferation and bring about the apoptosis of the cancerous cells. Combination of anticancer drugs with the Immunostimulatory drugs such as IMS-6 in the present invention is of added advantage due to the surge in proinflammatory cytokine TNF-α which hastens the process of apoptosis of the flagged cancerous cells. Further, enhanced non-specific immune response under the influence of the immune potentiators will lead to the increased macrophage activity thereby hastening the process of phagocytosis of the apoptosed cells and help in clearing the debris. The immunostimulant, IMS-6 may be given as adjuvant dose ranging from 250 mg to 500 mg in the form of syrup, tablet, capsule etc. in cancer patients along with prescribed anticancer drugs for the above immunostimulatory benefits.

In HIV, the cell-mediated immunity is affected due to consistent death of cells CD4+ and CD8+ cells and is characterized by reduced count of these cells responsible for fighting against the invading pathogen. IMS-6 with its Immunostimulatory properties will be of help in such situations to increase the cell-mediated immunity by initiating the clonal expansion of the lymphocytes. IMS-6 may be used in AIDS patients as syrup, tablet, and capsule etc. consisting of active dose of 250 mg to 1.0 g.

In situations of Hepatitis B and other viral infections, a potent antiviral drug with an Immunostimulatory agent like IMS-6 in the form of syrup, tablet, capsule etc. dose ranging from 250 mg to 500 mg will help in increasing the cell-mediated response and Humoral response to combat the viral infections and help in scavenging of the affected cells. Further, the enhanced levels of non-specific and specific immunity will also help in preventing the possibility of co-infection with bacterial or other viral agents.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. A natural immunostimulant composition comprising an extract of plant *Symplocos racemosa* and an extract of plant *Prosopis glandulosa* and a pharmaceutically acceptable carrier, wherein the extract of plant *Symplocos racemosa* is a water extract of plant *Symplocos racemosa* and of the extract of plant *Prosopis glandulosa* is a water extract of plant *Prosopis glandulosa*.

2. The natural immunostimulant composition according to claim 1, wherein the extract is obtained from all parts of said plant *Symplocos racemosa* and said plant *Prosopis glandulosa*.

3. The natural immunostimulant composition according to claim 1, wherein the extract is obtained from the leaves of plant *Prosopis glandulosa*.

4. The natural immunostimulant composition according to claim 1, wherein the extract is obtained from the barks of plant *Symplocos racemosa*.

5. The natural immunostimulant composition according to claim 1, the natural immunostimulant composition comprising water extracts of equimolar mixture of powders of leaves of plant *Prosopis glandulosa* and bark of plant *Symplocos racemosa*.

6. A pharmaceutical composition comprising a therapeutically effective amount of an extract of plant *Symplocos racemosa* and an extract of plant *Prosopis glandulosa*, the therapeutically effective amount of extract comprising at least one of alkaloids, bitters, glycosidic compounds, tannins, lipids, polysaccharides, flavonoids and terpenoid glycosides, wherein the extract of plant *Symplocos racemosa* is a water extract of plant *Symplocos racemosa* and the extract of plant *Prosopis glandulosa* is a water extract of plant *Prosopis glandulosa*.

7. The pharmaceutical composition according to claim 6, wherein the composition is in an oral dosage form.

8. A pharmaceutical composition comprising a therapeutically effective amount of extract of plant *Symplocos racemosa* and plant *Prosopis glandulosa* according to claim 7, wherein the composition comprises the extract in an amount ranging from about 5 mg to about 500 mg.

9. The pharmaceutical composition of claim 6, the pharmaceutical composition comprising water extracts of equimolar mixture of powders of leaves of plant *Prosopis glandulose* and bark of plant *Symplocos racemosa*.

10. A delivery system comprising a pharmaceutical composition comprising a therapeutically effective amount of an extract of plant *Symplocos racemosa* and an extract of plant *Prosopis glandulosa*, wherein the extract of plant *Symplocos racemosa* is a water extract of plant *Symplocos racemosa* and the extract of plant *Prosopis glandulosa* is a water extract of plant *Prosopis glandulosa*, wherein the delivery system is selected from the group consisting of tablets, capsules, pills, granules, powders, concentrates, syrups, and combinations thereof.

11. The delivery system according to claim 10, wherein the delivery system is a syrup.

12. The delivery system according to claim 11, wherein the syrup comprises a therapeutically effective amount of extract of plants *Symplocos racemosa* and *Prosopis glandulosa* in an amount of 50 mg to 500 mg and pharmaceutically acceptable carriers comprising 3.4 to 3.75 gm of sucrose, 0.01 to 0.02mg of citric acid, 0.01 mg of methyl paraben sodium, 0.0025 mg of propyl paraben sodium, 0.005 mg of strawberry flavor and sufficient amount of demineralized water to make up the volume to 5 ml of dosage form.

13. The delivery system according to claim 10, wherein the delivery system is a tablet.

14. The delivery system according to claim 13, wherein the tablet comprises granules of the extract of plant *Symplocos racemosa* and plant *Prosopis glandulosa*, and pharmaceutically acceptable excipients comprising about 30 mg of sodium starch glycolate, about 14 mg of calcium carbonate, about 3 mg of colloidal silicon dioxide and about 3 mg of magnesium stearate per 550 mg to 950 mg of the tablet.

15. The delivery system according to claim 14, wherein said granules comprise the extract of plant *Symplocos racemosa* and plant *Prosopis glandulosa* in an amount of 50 to 500 mg, and pharmaceutically acceptable carriers comprising 100 to 450 mg of microcrystalline cellulose, about 50 mg of pregelatinized starch, 50 to 300 mg of lactose, 50 to 250 mg of dibasic calcium phosphate, and sufficient amount of demineralized water to prepare per 500 to 900 mg of the granules.

16. A delivery system for orally administering the pharmaceutical composition according to claim 10, wherein the delivery system is a capsule.

17. The delivery system according to claim 16, wherein the capsule comprises granules of the extract of plant *Symplocos racemosa* and plant *Prosopis glandulosa* and pharmaceutically acceptable excipients comprising about 2 mg of colloidal silicon dioxide and about 3 mg of magnesium stearate per 305 mg to 505 mg of the capsule.

18. The delivery system according to claim 17, wherein said granules comprise the extract of plant *Symplocos racemosa* and plant *Prosopis glandulosa* in an amount of 50 to 250 mg, and pharmaceutically acceptable carriers comprising 100 to 450 mg of microcrystalline cellulose, about 50 mg of pregelatinized starch, 50 to 300 mg of lactose, 50 to 250 mg of dibasic calcium phosphate, and sufficient amount of demineralized water to prepare 300 to 500 mg of the granules.

19. The pharmaceutical composition of claim 10, the pharmaceutical composition comprising extracts of equimolar mixture of powders of leaves of plant *Prosopis glandulosa* and bark of plant *Symplocos racemosa*.

* * * * *